United States Patent [19]
Lazzara et al.

[11] Patent Number: 5,899,695
[45] Date of Patent: * May 4, 1999

[54] ANATOMIC INTERCHANGEABLE HEALING ABUTMENT AND IMPRESSION COPING

[76] Inventors: Richard J. Lazzara, 1814 "R" St., Lake Worth, Fla. 33460; Keith D. Beaty, 3 Old Meadow Way, Palm Beach Gardens, Fla. 33418

[ * ] Notice: This patent issued on a continued prosecution application filed under 37 CFR 1.53(d), and is subject to the twenty year patent term provisions of 35 U.S.C. 154(a)(2).

[21] Appl. No.: 08/337,387

[22] Filed: Nov. 8, 1994

[51] Int. Cl.⁶ ........................................... A61C 8/00
[52] U.S. Cl. ................................................. 433/173
[58] Field of Search ..................... 433/172, 173, 433/174, 175, 176

[56] References Cited

U.S. PATENT DOCUMENTS

| | | |
|---|---|---|
| 4,758,161 | 7/1988 | Niznick . |
| 4,850,870 | 7/1989 | Lazzara et al. . |
| 4,850,873 | 7/1989 | Lazzara et al. . |
| 4,856,994 | 8/1989 | Lazzara et al. . |
| 4,955,811 | 9/1990 | Lazzara et al. . |
| 4,988,298 | 1/1991 | Lazzara et al. . |
| 5,006,069 | 4/1991 | Lazzara et al. . |
| 5,015,186 | 5/1991 | Detsch . |
| 5,030,096 | 7/1991 | Hurson et al. . |
| 5,035,619 | 7/1991 | Daftary . |
| 5,040,983 | 8/1991 | Binon . |
| 5,071,351 | 12/1991 | Green, Jr. et al. . |
| 5,073,111 | 12/1991 | Daftary . |
| 5,100,323 | 3/1992 | Friedman et al. . |
| 5,135,395 | 8/1992 | Marlin .................................. 433/173 X |
| 5,145,371 | 9/1992 | Jorneus . |
| 5,145,372 | 9/1992 | Daftary et al. . |
| 5,154,612 | 10/1992 | Carlsson et al. . |
| 5,188,800 | 2/1993 | Green, Jr. et al. . |
| 5,209,659 | 5/1993 | Friedman et al. . |
| 5,209,666 | 5/1993 | Balfour et al. . |
| 5,213,502 | 5/1993 | Daftary . |
| 5,246,370 | 9/1993 | Coatoam . |
| 5,281,140 | 1/1994 | Niznick . |
| 5,292,252 | 3/1994 | Nickerson et al. . |
| 5,297,963 | 3/1994 | Daftary ................................... 433/172 |
| 5,316,476 | 5/1994 | Krauser . |
| 5,334,024 | 8/1994 | Niznick ............................... 433/172 X |
| 5,336,090 | 8/1994 | Wilson, Jr. et al. . |
| 5,338,196 | 8/1994 | Beaty et al. ............................ 433/172 |
| 5,362,235 | 11/1994 | Daftary ................................... 433/172 |
| 5,368,483 | 11/1994 | Sutter et al. . |
| 5,419,702 | 5/1995 | Beaty et al. . |
| 5,431,567 | 7/1995 | Daftary ................................... 433/172 |
| 5,476,382 | 12/1995 | Daftary ................................... 433/172 |
| 5,476,383 | 12/1995 | Beaty et al. . |
| 5,492,471 | 2/1996 | Singer .................................... 433/172 |
| 5,651,675 | 7/1997 | Singer .................................... 433/172 |
| 5,674,069 | 10/1997 | Osorio .................................... 433/172 |

FOREIGN PATENT DOCUMENTS 0 657 146 A1  6/1995  European Pat. Off. .

OTHER PUBLICATIONS

Exhibit A, a drawing of a healing abutment.
Exhibit B, an assembly drawing of a coping and the component drawings which comprise the coping assembly.
Geroge Perri, DDS et al., Single Tooth Implants, *CDA Journal*, vol. 17, No. 3, Mar. 1989.
DIA™ Dental Imaging Associates, Implamed—The Source, *The Anatomical Abutment System*, Copyright Date Oct. 9, 1991 on p. 10 (front cover, pp. 1–10, and back cover).
S.G. Lewis et al., Single Tooth Implant Supported Restorations, *Intnatl. Jrnl. of Oral & Maxillofacial Implants*, vol.3, No. 1, pp. 25–30, 1988.
S.G. Lewis et al., The "UCLA"Abutment, *Intnatl. Jrnl. of Oral & Maxillofacial Implants*, vol. 3, No. 3, pp. 183–189, 1988.

*Primary Examiner*—Nicholas D. Lucchesi
*Attorney, Agent, or Firm*—Arnold White & Durkee

[57] ABSTRACT

Dental restoration components for use to make a replacement tooth which substantially mimics the emergence profile of a natural tooth comprising two parts, one being a core adapted for fixation subgingivally in the site of the natural tooth, and the other being an emergence-profiler guide which fits on the core and shapes the overlying gingiva to the desired emergence profile. Two sets of the components may be provided, one for use as a healing abutment, and the other for use as an impression coping.

104 Claims, 2 Drawing Sheets

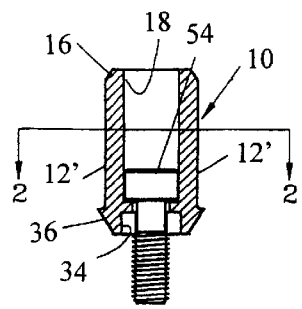
FIG. 1
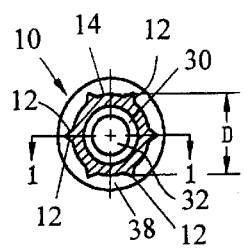
FIG. 2
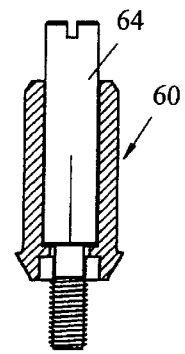
FIG. 6
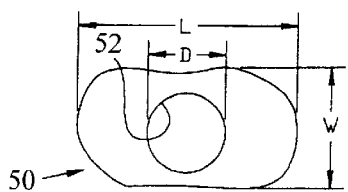
FIG. 4
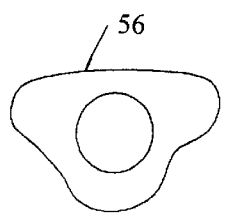
FIG. 5
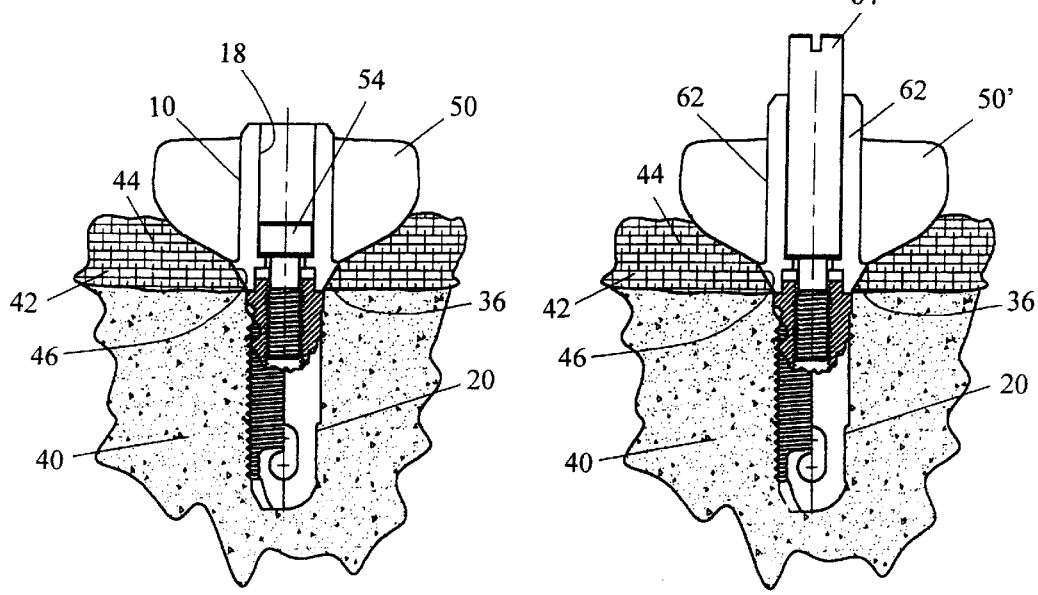
FIG. 3
FIG. 7

5,899,695

ANATOMIC INTERCHANGEABLE HEALING ABUTMENT AND IMPRESSION COPING

This invention relates to the art of preparing dental restorations that closely replicate natural dentition in appearance, contour and dimensions, especially where the teeth emerge from the gums. More particularly, this invention addresses the task of providing an improved emergence profile for an artificial tooth which will closely replicate the emergence profile of the natural tooth that it replaces no matter what the size and shape of the emergence profile of that tooth may have been. The invention of this application is related to the invention of application Ser. No: 08/043,928 filed Apr. 8, 1993 and allowed Feb. 14, 1994, both applications being commonly owned.

BACKGROUND OF THE INVENTION

For artificial teeth (commonly called "dental restorations") closely to replicate the lost natural teeth that they replace the artificial teeth must appear to emerge from the gums with the same shapes and contours that natural teeth have as they emerge from the gums. The increasing availability of dental implants, particularly osseointegrated implants, to serve as artificial roots, has provided opportunities to address this problem using techniques for fabricating implant-supported restorations directly to implants. Such a technique is described in published articles which appeared in The International Journal of Oral & Maxillofacial Implants, Vol. 3, Number 1, 1988 at pages 25–26 "Single-Tooth Implant Supported Restorations" Lewis, S. G. et al., and Number 3, 1988 at pages 183–189 "The "UCLA" Abutment", Lewis, S. et al. A similar result using a different abutment is described in U. S. Pat. No: 4,988,298, which is owned by the Assignee of the present invention. The problem is incompletely addressed in U. S. Pat. No: 5,073,522 issued to Daftary Dec. 17, 1991.

In general, the existing techniques are done using components which function to expand a transmucosal opening from the round size of the implant to a larger round size that more nearly approximates the size of the tooth where it emerges from the gum. The above-mentioned application Ser. No: 08/043,928 teaches a method and means to expand a transmucosal opening from the round size of the implant to a larger non-round size that more nearly approximates the size and the shape of the tooth where it emerges from the gum. The present invention further improves the art with a system of interchangeable components which enables low cost and convenient replication of the emergence profiles of all the different sizes and shapes of human teeth.

GENERAL NATURE OF THE INVENTION

Generally, the invention provides a pair of substantially identical core abutments, one to be used to support a healing abutment, and the other to be used to support an impression coping, together with a set of identical pairs of anatomic emergence-profiler healing abutment and impression coping formers, or guides, which are interchangeably mountable on the core abutments. Each set replicates the emergence profile of one type of natural tooth - e.g: molar, premolar, bicuspid, incisor, etc. The core abutments are made of a rigid material that can be made in precise dimensions, such as titanium. The emergence-profiler abutment and coping formers or guides are made of a low cost moldable material, such as a plastics material (e.g: acrylic) that is acceptable for dental use, and are preferably disposable, so that they can be used for one patient only and can if necessary be modified at chair-side. The emergence-profiler abutment guides replicate the emergence profile of the tooth that is to be restored, but they are made so short that they need not have occlusive surfaces, and the core abutments used to support them are similarly shortened. The emergence-profiler coping guides may be similarly short, in fact they may be identical to their corresponding emergence-profiler abutment guides, but the core abutments used to support the emergence-profiler coping guides may be longer for engagement in the materials used to take impressions, and may be fitted with means to retain them in the impression material. The invention has as its principal object to provide low-cost, reliable and precise method and means to realize the invention of the above-mentioned application Ser. No: 08/043,928. Like the invention of that application, the invention of the present application can be used to make stone models and soft tissue models of a patient's case.

BRIEF DESCRIPTION OF THE DRAWINGS

FIG. 1 is a longitudinal section through a core abutment according to the invention;

FIG. 2 is a transverse section through FIG. 1;

FIG. 3 is a side view of a healing abutment assembled on a dental implant;

FIG. 4 is a top view of a emergence-profiler component of the invention;

FIG. 5 is a top view of another emergence profiler component;

FIG. 6 is a longitudinal section through a core abutment for use as a pick-up type transfer coping;

FIG. 7 is a side view of a pick-up type transfer coping assembled on a dental implant;

DETAILED DESCRIPTION OF THE DRAWINGS

Figure 8:
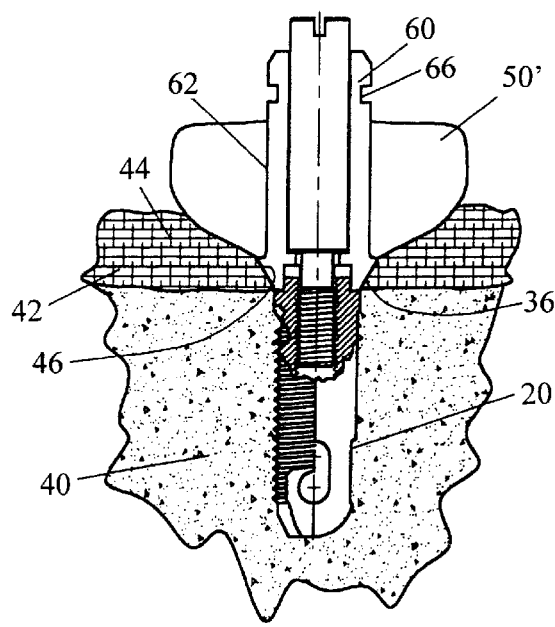
FIG. 8 is another embodiment of a pick-up transfer coping.

Referring first to FIGS. 1 to 3, a core component 10 is generally tubular in form with an outer diameter "D" substantially the same as the diameter of the implant 20 (FIG. 3) on which it is to be mounted. Longitudinally-oriented ribs 12 are on the outer surface 14 which defines the diameter "D". Preferably, the ribs 12 have sharp edges 12', seen in FIG. 1. The ends 16 of the ribs at the supragingival end 18 of the core component are sloped toward the sharp edges. Six ribs are illustrated in FIG. 2, but the number of ribs can be different. In other structural respects that are illustrated in the drawings, the core components are similar to known abutments; that is, the transverse member 30 defining a screw hole 32 and the top surface of a hexagonal socket 34, and the expanded subgingival end 36 with its shoulder 38, are known features of existing abutments.

In FIG. 3 the core component 10 is shown installed on a dental implant 20 which is fixed in bone 40 having overlying gingiva 42 with an aperture 46 giving access to the implant. As is the prevailing dental practice, the implant is substantially entirely encased in the bone, and the subgingival end 36 is mated to the implant, through the aperture, within the gingiva, at the junction of the gingiva and the bone. The emergence profile to be given to the aperture 46 through the gingiva will depend on the type of tooth that was in the site where the implant is now installed. FIGS. 3 and 4 illustrate a molar-type emergence-profiler abutment guide 50, for use as a healing component, having a mesial-distal distal dimension "L" and a buccal-labial dimension "W" which are characteristic of that type. A hole 52 through this abutment guide has the same diameter "D" as the core component 10. In use the healing component 50 is forced over the core component 10 so that the ribs 12 become embedded in the walls of the hole 52 until the healing component is seated on the shoulder 38. The assembly of both components is then attached to the implant in known fashion, using an abutment screw 54. The core component 10 is thereby fixed non-rotatively on the implant 20, and the healing component 50 is thereby fixed non-rotatively on the core component.

As is apparent in FIGS. 3 and 4, the healing component is now fixed in a position to force the aperture 46 to heal in a contour which closely replicates the emergence profile of a premolar-type tooth. FIG. 5 illustrates an alternative healing component 56 that can be used for restoration of another type tooth. It will be apparent that pairs of such tooth-shaped components can be provided at low cost in a wide variety of shapes, contours and sizes for a wide variety of tooth types.

Referring now to FIGS. 6 and 7, the invention is there illustrated as it may be used to take an impression preparatory to making a laboratory model. A core abutment 60 intended for use as a pick-up type impression coping is longer than the core abutment 10, and a pick-up type coping screw 64 replaces the abutment screw 54. Otherwise the two core abutments are substantially identical. In use, the healing component 50 and its core component 10 are removed together, as a unit, from the implant 20, the longer core abutment 60 is non-rotatively attached to the implant with the coping screw, and a second premolar-type emergence-profiler guide 50', intended for use as an impression coping component, which may be identical to the first premolar-type component 50, is fitted over the core abutment 60 engaging the ribs 62 while oriented identically to the healing component 50. This assembly 50'–60 can then function as a pick-up impression coping in know fashion. The protruding supragingival end of the core component 60, together with the portion of the emergence-profiler guide 50' which extends above the gum 44, will serve to retain the coping in the impression material (not shown). The coping screw 64 will extend through the impression tray (not shown) where it can be accessed to separate the impression coping assembly 50'–60 from the implant, allowing the coping assembly to be "picked-up", or retained in the impression for use in making a model of the site.

Figure 9:
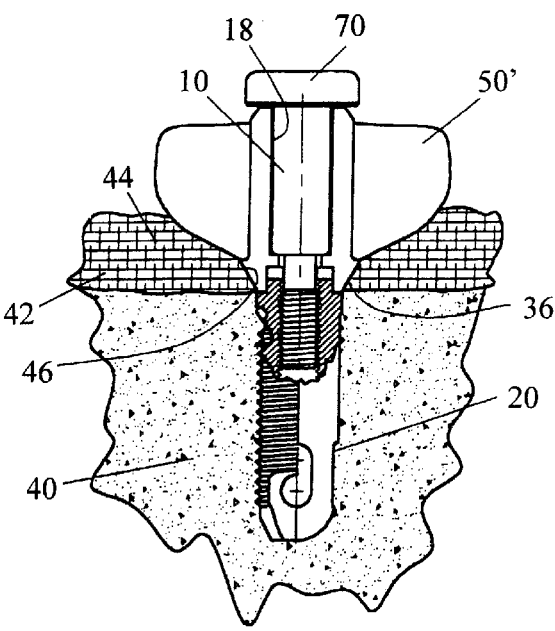
FIG. 9 shows another transfer coping according to the invention.
Figure 10:
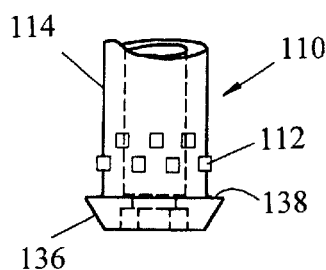
FIG. 10 is a side view of another core component.
Figure 11:
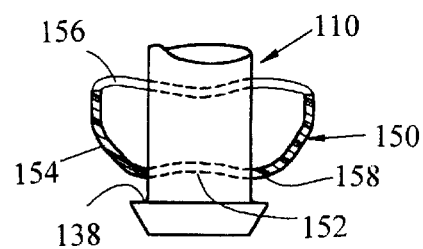
FIG. 11 is a section through another embodiment of the profiler guide.

Additional means to retain the pick-up coping assembly in impression material may be provided, in the form of an annular groove 66 on the core abutment 60, as is shown in FIG. 8, for example. In this embodiment, the groove 66 is preferably located closely above the top surface of the impression coping component 50', where impression material that flows into the groove can serve to lock the coping component 50' in place on the core abutment. Another alternative is to employ the shorter abutment 10 with a wide-headed impression-coping screw 70, like that shown in pat. no. 4,955,811 owned by the assignee of this application, as is illustrated in FIG. 9. In this embodiment the transfer coping that results is not a pick-up coping. FIGS. 10 and 11 illustrate another embodiment of the invention employing a hollow-shell form 154 to make the emergence-profiler guide member 150 of the invention. The shell form can be, for example, blow-molded of a plastics material with an outer shape and contour to mimic a natural tooth. The shell has a round hole 152 in its bottom 158 through which a core component 110 can pass. Like the bore 52 in FIG. 4, this hole 152 has a diameter sized to fit closely around the core component. In use the shell 154 is fitted onto the core component 110 with its bottom 158 seated on the shoulder 138 on the subgingival end 136 and the shell is then filled, preferably to its rim 156, around the tubular part of the core component, with a flowable filling material such as an acrylic (not shown) intended for dental use, which hardens to form a substantially solid body within the shell, thereby providing a substantially solid emergence-profiler guide. The use of a flowable filling material allows the core component 110 to have multi-dimensional locking means such as projections 112 on its outer surface 114. Except for this unique difference the core component may be identical to the core components 10 or 60.

The invention thereby provides a new, accurate and inexpensive method and means for making and using an impression coping that faithfully reproduces the emergence profile established in the gingiva by the healing abutment component, and that can faithfully and accurately transfer that information to a working model in order to build an anatomically-shaped artificial tooth on a round-shaped implant.

The invention lends itself to the provision of temporary dentition. For example, the healing abutment can also function as a temporary tooth, albeit one lacking an occlusal surface. If an occlusal surface is desired the dentist can provide one by adding temporary tooth material (e.g: acrylic) to the top surface of the emergence-profiler guide 50.

We claim:

1. A dental healing component for mounting on a root means located within a jawbone and exposed through an aperture in overlying gingiva, said aperture generally mimicking an emergence profile of a natural tooth, said healing component comprising:
    a core adapted for fixation subgingivally on said root means;
    means for fixing said core subgingivally on said root means through said aperture in said overlying gingiva;
    an emergence-profiler healing guide having an exterior surface contoured to provide said emergence profile in said aperture, said exterior surface being made of a plastic material; and
    means for fixing said emergence-profiler healing guide to said core with said exterior surface located in said aperture.

2. The dental healing component according to claim 1 in which said core is substantially tubular and said emergence-profiler healing guide has a substantially cylindrical bore enabling said emergence-profiler healing guide to fit telescopically on said core.

3. The dental healing component according to claim 2 in which said core has engagement means on an outer surface thereof for engaging a wall of said bore for holding said emergence-profiler healing guide against rotation on said core around a tubular axis thereof.

4. The dental healing component according to claim 3 in which said emergence-profiler healing guide is made of a material which is softer than a material of said core.

5. The dental healing component according to claim 4 in which said core is made of a metal and said emergence-profiler healing guide is made entirely of a plastic material.

6. The dental healing component according to claim 5 in which said emergence-profiler healing guide has a non-circular external shape substantially approximating a general shape of said natural tooth.

7. The dental healing component according to claim 3 in which said engagement means comprises at least one longitudinal rib extending radially outward from said outer surface.

8. The dental healing component according to claim 7 in which said at least one longitudinal rib has a sharp edge at a radial extremity.

9. The dental healing component according to claim 1 in which said emergence-profiler healing guide has a non-circular external shape substantially approximating a general shape of said natural tooth.

10. The dental healing component according to claim 1 in which said plastic material is acrylic.

11. The dental healing component according to claim 1 in which said core has a surface forming a portion of said emergence profile.

12. The dental healing component according to claim 1 in which said emergence-profiler healing guide is made entirely of a plastic material.

13. A set of dental healing components for forming an aperture in gingiva generally mimicking a contour and dimensions of an emergence profile of a natural tooth through said gingiva, said set of healing components being adapted for fixation on root means located in a jawbone and exposed through said aperture, said set comprising:

at least one core for extending subgingivally through said aperture and including means to fix said at least one core on said root means through said aperture in said gingiva; and a plurality of emergence-profiler healing guides each having an exterior surface being made of a plastic material and being contoured and dimensioned substantially to form said emergence profile in said aperture, each of said plurality of emergence-profiler healing guides for fitting around and engaging said at least one core, at least one of said plurality of emergence-profiler healing guides having a different cross-sectional shape of said exterior surface than remaining ones of said plurality of emergence-profiler healing guides.

14. The set of dental healing components according to claim 13 in which another of said remaining ones of said plurality of emergence-profiler healing guides has another different shape on said exterior surface than the rest of said remaining ones.

15. The set of dental healing components according to claim 13 in which a cross-section through said exterior surfaces is generally non-round.

16. The set of dental healing components according to claim 13 in which at least one of said plurality of emergence-profiler healing guides has a same cross-sectional shape but a different cross-sectional dimension through said exterior surface than remaining ones of said plurality of emergence-profiler healing guides.

17. The set of dental healing components according to claim 13 in which said at least one core has on an outer surface means for restraining one of said plurality of emergence-profiler healing guide from rotating around a tubular axis of said core.

18. The set of dental healing components according to claim 13 in which at least one of said plurality of emergence-profiler healing guides is made entirely of a plastic material.

19. The set of dental healing components according to claim 13 in which said plastic material is acrylic.

20. The set of dental healing components according to claim 13 in which said plurality of emergence-profiler healing guides includes a shell and a filling material disposed within said shell around one of said at least one core.

21. The set of dental healing components according to claim 20 in which at least one of said plurality of emergence-profiler healing guides has an exterior surface with a same cross-sectional shape but a different cross-sectional dimension than remaining ones of said plurality of emergence-profiler healing guides.

22. The set of dental healing components according to claim 20 in which said filling material is acrylic.

23. The set of dental healing components according to claim 20 in which said at least one core includes means for locking said filling material therearound.

24. The set of dental healing components according to claim 23 in which said locking means is a plurality of projections extending from an outer surface of said at least one core.

25. The set of dental impression components for making a model to produce a prosthodontic restoration intended to be fitted on an end surface of a dental implant being embedded in a jawbone and being exposed through an aperture in gingiva overlying said jawbone, said aperture generally mimicking a contour and dimensions defining an emergence profile of a natural tooth, said set comprising:

at least one core for extending through said aperture, and including means to fix said at least one core on said dental implant; and a plurality of emergence-profiler coping guides each having an exterior surface being made of a plastic material and contoured and dimensioned substantially to fit within said aperture, each of said plurality of emergence-coping guides being adapted for fitting around and engaging said at least one core, at least one of said plurality of emergence-profiler coping guides having a different cross-sectional shape of said exterior surface than remaining ones of said plurality of emergence-profiler coping guides.

26. The set of dental impression components according to claim 25 in which another of said remaining ones of said plurality on emergence-profiler coping guides has another different cross-sectional shape on said exterior surface than the remaining ones of said plurality of emergence-profiler coping guides.

27. The set of dental impression components according to claim 25 in which at least one of said plurality of emergence-profiler coping guides has a same cross-sectional shape but a different cross-sectional dimension of said exterior surface than remaining ones of said plurality of emergence-profiler coping guides.

28. The set of dental impression components according to claim 25 in which said plastic material is acrylic.

29. The set of dental impression components according to claim 25 in which said at least one core has on an outer surface means for restraining each of said set of emergence-profiler coping guides from rotating therearound.

30. The set of dental impression components according to claim 25 in which said shapes are non-round.

31. The set of dental impression components according to claim 25 in which said plurality of emergence-profiler coping guides includes a shell and a filling material placed within said shell around one of said at least one core.

32. The set of dental impression components according to claim 31 in which another of said remaining ones of said plurality of emergence-profiler coping guides has another different cross-sectional shape of said exterior surface than the remaining ones of said emergence-profiler coping guides.

33. The set of dental impression components according to claim 31 in which said at least one core includes means for locking the filling material thereon.

34. The set of dental impression components according to claim 33 in which said locking means includes projections extending outwardly from an outer surface of said at least one core.

35. The set of dental impression components according to claim 31 in which said filling material is made of a plastic material.

36. The set of dental impression components according to claim 31 in which said plastic material is acrylic.

37. The set of dental impression components according to claim 25 in which said at least one core includes at least one longitudinal rib.

38. A method of preparing an artificial tooth for placement on root means at a site in a jawbone, said site having an overlying gingiva layer having an aperture to said root means, said method comprising the steps of:

fixing a first end of an elongated first core subgingivally on said root means through said aperture in said overlying gingiva layer;

providing a emergence-profiler healing guide having an exterior surface contoured and dimensioned substantially to form an emergence profile in said aperture, said exterior surface being made of a plastic material;

attaching said emergence-profiler healing guide to said elongated first core with said exterior surface located in said aperture positioned to guide said overlying gingiva layer to heal substantially in the general shape of said emergence profile;

removing said first core and said emergence-profiler healing guide after said overlying gingiva layer is healed;

fixing a first end of an elongated second core subgingivally on said root means through said aperture healed in said general shape;

providing an emergence-profiler coping guide having an exterior surface contoured and dimensioned substantially identically to said exterior surface of said emergence-profiler healing guide; and attaching said emergence-profiler coping guide to said second core in position to substantially fit within said aperture healed in said general shape.

39. The method according to claim 38 including the further steps of making an impression of said site with said second core and said emergence-profiler coping guide fixed on said root means, and thereafter with said second core and said emergence-profiler coping guide fixed in said impression making a model of said site with said aperture healed in said general shape.

40. The method according to claim 38 wherein at least one of said emergence-profiler healing and coping guides includes a shell configuration and said method comprising the further steps of:

fitting said shell configuration on said first or second respective core;

selecting a flowable filling material which subsequently becomes substantially hard; and filling said shell configuration with said flowable material around said first or second respective cores.

41. A method of shaping an opening in a patient's gingiva adjacent to a dental implant installed in the patient's jawbone, said method comprising the steps of:

providing a set of healing components, said set of healing components including at least one core and a plurality of emergence-profiler healing guides having different shapes corresponding to shapes of a transmucosal portions of different natural teeth, each of said plurality of emergence-profiler healing guides having an exterior surface being made of a plastic material;

selecting from said set of healing components an emergence-profiler healing guide having a shape corresponding to said shape of the transmucosal portion of a natural tooth being replaced;

fixing said at least one core to said dental implant;

attaching said selected emergence-profiler healing guide to said at least one core; and allowing said patient's gingiva to heal around said selected emergence-profiler healing guide so as to shape said opening.

42. The method of claim 41 wherein said plurality of emergence-profiler healing guides have shapes corresponding to at least molar, premolar, bicuspid and incisor teeth.

43. The method of claim 41 wherein said step of attaching said selected emergence-profiler healing guide to said at least one core includes the steps of:

inserting said at least one core through a hole in said emergence-profiler healing guide; and engaging a wall defining said hole with a rotational-prohibiting structure located on said at least one core.

44. The method of claim 41 further including the step of:

manually altering said selected emergence-profiler healing guide to conform to said shape of said natural tooth.

45. The method of claim 41 wherein said step of attaching said selected emergence-profiler healing guide to said at least one core includes the step of engaging a shoulder of said at least one core with a bottom side of said emergence-profiler healing guide.

46. The method of claim 41 wherein said plurality of emergence-profiler healing guides and said at least one core do not have occlusive surfaces.

47. The method of claim 41 wherein said set of healing compounds each is a shell and said method further includes the step of:

filling said shell with a material to produce a solid emergence-profiler healing guide.

48. The method of claim 47 further including the steps of:

heating said material to a flowable state; and inserting said flowable material through an opening at a top region of said emergence-profiler healing guide.

49. The method of claim 47 wherein said material is a polymer.

50. A dental healing component for forming an aperture in overlying gingiva generally mimicking an emergence profile of a natural tooth, said healing component being adapted for fixation in root means within a jawbone comprising:

a core adapted to extend through said aperture in said overlying gingiva;

means for attaching said core subgingivally on said root means;

an emergence-profiler healing guide including a shell with a plastic outer surface contoured to form said emergence profile in said aperture and a filling material disposed within said shell around said core; and means for locating said emergence-profiler healing guide around said core.

51. The dental healing component of claim 50 in which said shell is made entirely of a plastic material.

52. The dental healing component of claim 50 in which said core is substantially tubular and said emergence-profiler healing guide has a substantially cylindrical bore enabling said emergence-profiler healing guide to fit telescopically on said core.

53. The dental healing component of claim 52 in which said core has means on its exterior surface for engaging a wall defining said bore and for holding said emergence-profiler healing guide against rotation on said core.

54. The dental healing component of claim 53 in which said engaging and holding means are structural projections extending outwardly from said exterior surface.

55. The dental healing component of claim 54 in which said engaging and holding means include at least one longitudinal rib.

56. The dental healing component of claim 55 in which said at least one longitudinal rib has a sharp edge at a radial extremity.

57. The dental healing component of claim 56 in which an end of said at least one longitudinal rib adjacent to a supragingival end of said core is sloped toward said sharp edge.

58. The dental healing component of claim 50 in which said core is metal and said emergence-profiler healing guide is made entirely of plastic material.

59. The dental healing component of claim 50 in which said emergence-profiler healing guide has a non-round external shape generally in a shape of said natural tooth.

60. The dental healing component of claim 50 in which said filling material is flowable when placed in said shell and thereafter hardens to form a substantially solid body within said shell.

61. The dental healing component of claim 60 in which said solid body is retained by said core.

62. The dental healing component of claim 50 in which said filling material is made of a plastic material.

63. The dental healing component of claim 62 in which said plastic material is acrylic.

64. The dental healing component of claim 50 in which said locating means further includes means for fixing said emergence-profiler healing guide on said core.

65. A dental impression coping for use in fabricating a model at a site in a jawbone containing a root means and overlying gingiva, said overlying gingiva having an aperture to said root means, said impression coping comprising:

a core adapted to extend through said aperture in said overlying gingiva;

means for attaching said core subgingivally around said root means;

an emergence-profiler coping guide including a shell with a plastic outer surface contoured and dimensioned to substantially fit within said aperture and a filling material in said shell around said core; and means for locating said emergence-profiler coping guide around said core with said plastic outer surface located in said aperture.

66. The impression coping of claim 65 wherein said locating means includes a hole in said emergence-profiler coping guide, an internal shape of said hole being substantially the same as an outer shape of said core.

67. The impression coping of claims 66 in which said core has on an outer surface means for restraining said emergence-profiler coping guides from rotating around a tubular axis of said core.

68. The impression coping of claim 65 in which said core includes a surface that conforms to substantially fit within a section of said aperture.

69. The impression coping of claim 65 in which said impression coping is a transfer coping.

70. The impression coping of claim 69 in which said attaching means of said core to said root means is a wide-headed impression-coping screw.

71. The impression coping of claim 65 in which said impression coping is a pick-up coping.

72. The impression coping of claim 71 which said core extends above said emergence-profiler coping guide.

73. The impression coping of claim 65 in which said locating means include means for fixing said emergence-profiler coping guide on said core.

74. The impression coping of claim 65 in which said core is rigid.

75. A dental impression coping for use in fabricating a model at a site in a jawbone containing a root means and overlying gingiva, said overlying gingiva having an aperture to said root means, said impression coping comprising:

a core adapted to extend through said aperture in said overlying gingiva, said core connecting to said root means; and an emergence-profiler coping guide including a shell with a plastic outer surface contoured and dimensioned to substantially fit within said aperture and a filling material in said shell around said core, said emergence-profiler coping guide surrounding and engaging said core.

76. The dental impression coping of claim 75 wherein said core has at least one projection around which said filling material is formed.

77. A dental impression coping for use in fabricating a model at a site in a jawbone containing a root means and overlying gingiva, said overlying gingiva having an aperture to said root means, said impression coping comprising:

a core adapted to extend through said aperture in said overlying gingiva;

means for fixing said core subgingivally on said root means;

an emergence-profiler coping guide having an exterior surface contoured and dimensioned to substantially fit within said aperture, said exterior surface being made of a plastic material; and means for fixing said emergence-profiler coping guide to said core.

78. Impression coping of claim 77 in which said emergence-profiler coping guide has a hole therethrough, an internal shape of said hole being substantially the same as an outer shape of said core.

79. The impression coping of claim 78 in which said core has on an outer surface means for restraining said emergence-profiler coping guides from rotating around a tubular axis of said core, said core having a cylindrical external shape.

80. The impression coping of claim 77 in which said core includes a surface that conforms to generally fit within a section of said aperture.

81. The impression coping of claim 77 in which said impression coping is a transfer coping.

82. The impression coping of claim 81 in which said means for fixing said core to said emergence-profiler coping guide is a wide-headed impression-coping screw.

83. The impression coping of claim 77 in which said impression coping is a pick-up coping.

84. The impression coping of claims 83 in which said core extends above said emergence-profiler coping guide.

85. The impression coping of claim 84 in which said core has means for connecting said core to impression material, said connecting means including a groove.

86. A dental impression coping for use in fabricating a model at a site in a jawbone containing a root means and overlying gingiva, said overlying gingiva having an aperture to said root means, said impression coping comprising:

a core adapted to extend through said aperture in said overlying gingiva, said core connecting to said root means; and an emergence-profiler coping guide including an exterior surface contoured and dimensioned to substantially fit within said aperture, said exterior surface being made of a plastic material, said emergence-profiler coping guide surrounding and engaging said core.

87. The dental impression coping of claim 86 wherein said core has a structure for fixing said emergence-profiler coping guide against rotation.

88. A method of forming an impression for making a replacement tooth mimicking a contour and dimensions of an emergence profile of a natural tooth in a site in a living jawbone, said living jawbone having a root means and an aperture through overlying gingiva to said root means, said method comprising the steps of:

providing at least one core and a set of impression coping formers having exterior surfaces made of a plastic material, each of said set of impression coping formers has a central cavity for surrounding said at least one core, at least one of said set of impression coping formers having an exterior surface with a different shape than remaining ones of said set of impression coping formers;

fixing said at least one core on a dental implant so that said at least one core extends through said aperture;

selecting from said set of impression coping formers a former having substantially a same shape as said aperture;

mounting said selected former on said core attached to said implant; and taking said impression of said site.

89. The method of claim 88 which includes the additional step of making a stone model from said impression.

90. The method of claim 88 wherein said core is rigid.

91. The method of claim 88 wherein said step of mounting said selected former includes the steps of sliding said selected former over said core with said central cavity engaging said core.

92. The method of claim 88 wherein each of said set of impression coping formers include a shell and a filling material to be placed within said shell around said core.

93. The method of claim 92 wherein said step of mounting said selected former includes the step of filling said shell with said filling material and hardening said filling material.

94. The method of claim 93 wherein said filling material is a plastic material.

95. A dental healing component for mounting on a root means located within a jawbone and exposed through an aperture in overlying gingiva, said aperture generally mimicking an emergence profile of a natural tooth, said healing component comprising:

an emergence-profiler healing guide being made entirely of a plastic material and having an exterior surface contoured to form said emergence profile in said aperture, said emergence-profiler healing guide having a wall defining a substantially cylindrical bore;

a core adapted for fixation subgingivally on said root means, said core having a tubular section being received by said substantially cylindrical bore of said emergence-profiler healing guide and having means on an outer surface thereof for engaging said wall defining said substantially cylindrical bore and holding said emergence-profiler healing guide against rotation thereon, said engaging means including at least one longitudinal rib extending radially outward from said outer surface and having a sharp edge at a radial extremity, said core having a surface forming a portion of said emergence profile in said aperture; and a component for fixing said core on said root means.

96. A dental healing component for forming an aperture in gingiva generally mimicking an emergence profile of a natural tooth, said healing component being adapted for fixation in root means within a jawbone comprising:

an emergence-profiler healing guide being made entirely of a plastic material and having an exterior surface contoured to form said emergence profile in said aperture, said emergence-profiler healing guide including a shell contoured to form said emergence profile in said aperture and a filling material disposed within said shell, said filling material being flowable when placed in said shell and thereafter hardening to form a substantially solid body with said shell, said shell having a substantially cylindrical hole therethrough;

a core adapted for fixation subgingivally on said root means, said core having a tubular section being received by said substantially cylindrical hole in said shell and having means on an outer surface thereof for engaging and fixing said filling material on said core, said engaging means including at least one projection extending radially outward from said outer surface, said core having a surface forming a portion of said emergence profile; and a component for fixing said core on said root means.

97. A dental impression coping for use in fabricating a model at a site in a jawbone containing a root means and overlying gingiva, said overlying gingiva having an aperture to said root means, said impression coping comprising:

an emergence-profiler coping guide being made entirely of a plastic material and having an exterior surface contoured and dimensioned to substantially fit within said aperture, said emergence-profiler coping guide having a wall defining a substantially cylindrical bore;

a core adapted for fixation subgingivally on said root means, said core having a tubular section being received by said substantially cylindrical bore of said emergence-profiler coping guide and having means on an outer surface thereof for engaging said wall defining said substantially cylindrical bore and holding said emergence-profiler coping guide against rotation thereon, said engaging means including at least one longitudinal rib extending radially outward from said outer surface and having a sharp edge at a radial extremity; and a component for fixing said core on said root means.

98. A dental impression coping for use in fabricating a model at a site in a jawbone containing a root means and overlying gingiva, said overlying gingiva having an aperture to said root means, said impression coping comprising:

an emergence-profiler coping guide being made entirely of a plastic material and having an exterior surface contoured and dimensioned to substantially fit within said aperture, said emergence-profiler coping guide including a shell contoured and dimensioned to substantially fit within said aperture and a filling material disposed within said shell, said filling material being flowable when placed in said shell and thereafter hardening to form a substantially solid body with said shell, said shell having a substantially cylindrical hole therethrough;

a core adapted for fixation subgingivally on said root means, said core having a tubular section being received by said substantially cylindrical hole in said shell and having means on an outer surface thereof for engaging and fixing said filling material on said core and holding said emergence-profiler coping guide against rotation thereon, said engaging means including at least one projection extending radially outward from said outer surface; and a component for fixing said core on said root means.

99. A set of dental healing components for forming an aperture in gingiva generally mimicking a contour and dimensions of an emergence profile of a natural tooth through said gingiva, said set of healing components being adapted for fixation on root means located in a jawbone and exposed through said aperture, said set comprising:

a plurality of emergence-profiler healing guides being made entirely of a plastic material and having an exterior surface contoured for forming said emergence profile in said aperture, said plurality of emergence-profiler healing guides having a wall defining a substantially cylindrical bore, at least one of said plurality of emergence-profiler healing guides having a different cross-sectional shape of said exterior surface than remaining ones of said plurality of emergence-profiler healing guides;

at least one core adapted for fixation subgingivally on said root means, said at least one core having a tubular section being received by said substantially cylindrical bore and having means on an outer surface thereof for engaging said wall defining said substantially cylindrical bore and for holding one of said plurality of emergence-profiler healing guides against rotation thereon, said engaging means includes at least one longitudinal rib extending radially outward from said outer surface and having a sharp edge at a radial extremity, said at least one core having a surface for forming a portion of said emergence profile; and a component for fixing said at least one core on said root means.

100. A set of dental healing components for forming an aperture in gingiva generally mimicking a contour and dimensions of an emergence profile of a natural tooth through said gingiva, said set of healing components being adapted for fixation on root means located in a jawbone and exposed through said aperture, said set comprising:

a plurality of emergence-profiler healing guides being made entirely of a plastic material and having an exterior surface contoured for forming said emergence profile in said aperture, each of said plurality of emergence-profiler healing guides including a shell contoured for forming said emergence profile in said aperture and a filling material disposed within said shell, said filling material being flowable when placed in said shell and thereafter hardening to form a substantially solid body with said shell, each of said shells of said plurality of emergence-profiler healing guides having a hole therethrough, at least one of said plurality of emergence-profiler healing guides having a different cross-sectional shape of said exterior surface than remaining ones of said plurality of emergence-profiler healing guides;

at least one core adapted for fixation subgingivally on said root means, said at least one core having a tubular section for being received by said hole in said shell and having means on an outer surface thereof for engaging and fixing said filling material on said at least one core and holding one of said plurality of emergence-profiler healing guides against rotation thereon, said engaging means includes at least one projection extending radially outward from said outer surface, said at least one core having a surface for forming a portion of said emergence profile; and a component for fixing said on least one core on said root means.

101. A set of dental impression components for making a model that produces a prosthodontic restoration intended to be fitted on an end surface of a dental implant being embedded in a jawbone and being exposed through an aperture in gingiva overlying said jawbone, said aperture generally mimicking a contour and dimensions defining an emergence profile of a natural tooth, said set comprising:

a plurality of emergence-profiler coping guides being made entirely of a plastic material and having an exterior surface contoured and dimensioned for substantially fitting within said aperture, each of said plurality of said emergence-profiler coping guides having a wall defining a substantially cylindrical bore;

at least one core adapted for fixation subgingivally on said root means, said at least one core having a tubular section for being received by said substantially cylindrical bore and having means on an outer surface thereof for engaging said wall defining said substantially cylindrical bore and holding each of said plurality of emergence-profiler coping guide against rotation thereon, said engaging means includes at least one longitudinal rib extending radially outward from said outer surface and having a sharp edge at a radial extremity; and a component for fixing said at least one core on said root means.

102. A set of dental impression components for making a model that produces a prosthodontic restoration intended to be fitted on an end surface of a dental implant being embedded in a jawbone and being exposed through an aperture in gingiva overlying said jawbone, said aperture generally mimicking a contour and dimensions defining an emergence profile of a natural tooth, said set comprising:

a plurality of emergence-profiler coping guides being made entirely of a plastic material and having an exterior surface contoured and dimensioned for substantially fitting within said aperture, each of said plurality of emergence-profiler coping guides including a shell contoured to substantially fit within said aperture and a filling material disposed within said shell, said filling material being flowable when placed in said shell and thereafter hardening to form a substantially solid body with said shell, each of said shells of said plurality of said emergence-profiler coping guides having a hole therethrough;

at least one core adapted for fixation subgingivally on said root means, said at least one core having a tubular section being received by said hole in said shell and having means on an outer surface thereof for engaging and fixing said filling material on said at least one core and holding each of said plurality of emergence-profiler coping guides against rotation thereon, said engaging means includes at least one projection extending radially outward from said outer surface; and a component for fixing said at least one core on said root means.

103. A set of dental components for making a replacement tooth generally mimicking a contour and dimensions of an emergence profile of a natural tooth through gingiva overlying root means, said gingiva having an aperture to said root means, each set comprising:

- an emergence-profiler healing guide being made entirely of a plastic material and having an exterior surface contoured to form said emergence profile in said aperture, said emergence-profiler healing guide having a wall defining a substantially cylindrical bore;
- a first core adapted for fixation subgingivally on said root means, said first core having a tubular section being received by said substantially cylindrical bore of said emergence-profiler healing guide and having means on an outer surface thereof for engaging said wall defining said substantially cylindrical bore and holding said emergence-profiler healing guide against rotation thereon, said engaging means including at least one longitudinal rib extending radially outward from said outer surface and having a sharp edge at a radial extremity, said first core having a surface forming a portion of said emergence profile in said aperture;
- a component for fixing said first core on said root means;
- an emergence-profiler coping guide being made entirely of a plastic material and having an exterior surface contoured and dimensioned to substantially fit within said aperture, said emergence-profiler coping guide having a wall defining a substantially cylindrical bore;
- a second core adapted for fixation subgingivally on said root means, said second core having a tubular section being received by said substantially cylindrical bore of said emergence-profiler coping guide and having means on an outer surface thereof for engaging said wall defining said substantially cylindrical bore and holding said emergence-profiler coping guide against rotation thereon, said engaging means including at least one longitudinal rib extending radially outward from said outer surface and having a sharp edge at a radial extremity; and
- a component for fixing said second core on said root means.

104. A set of dental components for making a replacement tooth generally mimicking a contour and dimensions of an emergence profile of a natural tooth through gingiva overlying root means, said gingiva having an aperture to said root means, each set comprising:

- an emergence-profiler healing guide being made entirely of a plastic material and having an exterior surface contoured to form said emergence profile in said aperture, said emergence-profiler healing guide including a shell contoured to form said emergence profile in said aperture and a filling material disposed within said shell, said filling material being flowable when placed in said shell and thereafter hardening to form a substantially solid body with said shell, said shell having a substantially cylindrical hole therethrough;
- a first core adapted for fixation subgingivally on said root means, said first core having a tubular section being received by said substantially cylindrical hole in said shell and having means on an outer surface thereof for engaging and fixing said filling material on said first core, said engaging means including at least one projection extending radially outward from said outer surface, said first core having a surface forming a portion of said emergence profile;
- a component for fixing said first core on said root means;
- an emergence-profiler coping guide being made entirely of a plastic material and having an exterior surface contoured and dimensioned to substantially fit within said aperture, said emergence-profiler coping guide including a shell contoured and dimensioned to substantially fit within said aperture and a filling material disposed within said shell, said filling material being flowable when placed in said shell and thereafter hardening to form a substantially solid body with said shell, said shell having a substantially cylindrical hole therethrough;
- a second core adapted for fixation subgingivally on said root means, said second core having a tubular section being received by said substantially cylindrical hole in said shell and having means on an outer surface thereof for engaging and fixing said filling material on said second core and holding said emergence-profiler coping guide against rotation thereon, said engaging means including at least one projection extending radially outward from said outer surface; and
- a component for fixing said second core on said root means.

* * * * *